(12) United States Patent  (10) Patent No.: US 8,491,508 B2
Smith et al.  (45) Date of Patent: Jul. 23, 2013

(54) DEVICE AND METHOD FOR STIMULATING THE MEIBOMIAN GLANDS OF THE EYELID

(75) Inventors: Walton F. Smith, Ranchester, WY (US); David Yakos, Bozeman, MT (US); Randy Larimer, Bozeman, MT (US)

(73) Assignee: Walton F. Smith, Ranchester, WY (US)

( * ) Notice: Subject to any disclaimer, the term of this patent is extended or adjusted under 35 U.S.C. 154(b) by 281 days.

(21) Appl. No.: 12/883,052

(22) Filed: Sep. 15, 2010

(65) Prior Publication Data

US 2012/0065556 A1   Mar. 15, 2012

(51) Int. Cl.
   *A61H 5/00*   (2006.01)

(52) U.S. Cl.
   USPC .............. 601/85; 601/18; 601/37; 601/84

(58) Field of Classification Search
   USPC ............ 601/15, 18, 89, 13, 46, 97–98, 101, 601/112, 116, 85; 607/96, 98, 108–109
   See application file for complete search history.

(56) References Cited

U.S. PATENT DOCUMENTS

| | | | |
|---|---|---|---|
| 4,387,707 A * | 6/1983 | Polikoff | 601/37 |
| 4,918,818 A | 4/1990 | Hsieh | |
| 5,925,002 A * | 7/1999 | Wollman | 601/70 |
| 5,974,615 A * | 11/1999 | Schwarz-Hartmann et al. | 15/22.4 |
| 6,275,735 B1 | 8/2001 | Jarding et al. | |
| 6,536,066 B2 * | 3/2003 | Dickie | 15/22.1 |
| 6,866,776 B2 * | 3/2005 | Leason et al. | 601/15 |
| 7,069,084 B2 | 6/2006 | Yee | |
| 7,122,013 B2 | 10/2006 | Liu | |
| 7,384,405 B2 | 6/2008 | Rhoades | |
| 7,637,878 B2 | 12/2009 | Lin | |
| 2002/0156402 A1 | 10/2002 | Woog et al. | |
| 2003/0233135 A1 | 12/2003 | Yee | |
| 2004/0035439 A1 * | 2/2004 | Lai et al. | 132/322 |
| 2005/0132513 A1 * | 6/2005 | Eliav et al. | 15/22.1 |
| 2006/0048314 A1 * | 3/2006 | Kressner | 15/22.1 |
| 2006/0058714 A1 | 3/2006 | Rhoades | |
| 2006/0200052 A1 | 9/2006 | Lin | |
| 2006/0206041 A1 | 9/2006 | Liu | |
| 2006/0211961 A1 * | 9/2006 | Meyer et al. | 601/73 |
| 2008/0109053 A1 * | 5/2008 | Grenon et al. | 607/109 |
| 2008/0132978 A1 * | 6/2008 | Korb et al. | 607/109 |
| 2008/0200848 A1 | 8/2008 | Avni | |
| 2009/0177125 A1 * | 7/2009 | Pilcher et al. | 601/18 |
| 2010/0160841 A1 * | 6/2010 | Wu | 601/135 |

* cited by examiner

*Primary Examiner* — Justine Yu
*Assistant Examiner* — Timothy Stanis
(74) *Attorney, Agent, or Firm* — Antoinette M. Tease

(57) ABSTRACT

A device for stimulating the meibomian glands of the eyelid comprising: a handle; a head that is non-removable and integral to the handle, the head comprising an eyepiece that oscillates to provide a massaging action to an eyelid and that comprises a front end that is concave in shape to fit over an eyelid; a heater located inside of the eyepiece; a temperature sensor located inside of the eyepiece, wherein the temperature sensor causes the eyepiece to heat to a predetermined temperature and then stop heating; and a charging base that supplies power to a motor that causes the eyepiece to oscillate, wherein the motor comprises a motor shaft. A method of applying heat and massaging action to the eyelid at the same time.

1 Claim, 13 Drawing Sheets

DEVICE AND METHOD FOR STIMULATING THE MEIBOMIAN GLANDS OF THE EYELID

BACKGROUND OF THE INVENTION

1. Field of the Invention

The present invention relates generally to the field of medical devices and, more specifically, to a handheld device that stimulates the meibomian gland of the eyelid both mechanically and thermally at the same time.

2. Description of the Related Art

Meibomian gland dysfunction, dry eye and chronic marginal eyelid inflammation are widespread problems, especially in middle age and geriatric populations worldwide. In fact, the problem is so widespread that this topic is covered in virtually every ophthalmic medical textbook and is the sole focus for groups of international researchers such as the Tear Film and Ocular Surface Society. The common cause of "dry eye" is not—as one might expect—a lack of watery substance in tears, but it is in most cases a lack of an oily substance in tears. Tears are a complex mix of substances from various glands located on and around the eye. These substances need to be in the correct balance in order to maintain the health of the eye and to preserve vision. The present invention deals with constant (or basal) tears and not with reflex tears (as in crying).

The tears of the eye are made from different elements. The majority of the tear film is thin fluid that comes from the lacrimal gland, which is located directly above the eye. The quantity and quality of this fluid is usually not the problem. The meibomian glands, which are located throughout both the upper and lower eyelids and number in the range of twenty per lid, secrete an oily material (lipids) that keeps the watery part of tears (i.e., the fluid secreted by the lacrimal gland), from evaporating. This material is normally secreted/expressed with each blink. It is the dysfunction of these glands that is the problem for most people who suffer from dry eye conditions.

In individuals with healthy tear secretion, the oily material secreted by the meibomian glands is relatively warm and runny. Like any oil, however, this material becomes more viscous as it cools. As the normal human ages, the outflow of the meibomian glands decreases, thereby reducing tear contact time and causing a marked decrease in tear quality. In some individuals with long-stand meibomian gland dysfunction, secretions may cease altogether. To some extent, this occurrence is due to the thinning of the skin and the cooling of the oily material in the glands due to loss of body heat. As a result, the oily material that should have the consistency of olive oil is instead semi-solid, like butter. When this happens, it is not easily secreted from the eyelid without being physically massaged (i.e., forced out as in squeezing toothpaste from a tube) and/or warmed up (to alter the consistency).

The most common treatment for this condition, referred to as meibomian gland disease or meibomianitis, consists of having the patient apply a warm, wet compress to the eye repeatedly until the lids are warm and pliable and then massaging the eye with the fingers or a homemade device such as a bag filled by uncooked rice grains. This procedure is messy and inconvenient and must be repeated daily in order to have the intended effects. Furthermore, it is difficult to achieve and maintain the optimum temperature. Physicians are also somewhat reluctant to use this technique for fear of an elderly patient burning himself or herself. Without an immediate improvement in symptoms, patients often become disenchanted and discontinue therapy.

There are various prescription and non-prescription medications, topical and oral, directed toward alleviating the effects of dysfunctional meibomian glands, and research efforts directed toward pharmaceutical solutions are ongoing. The appeal of the pharmaceutical remedies is that they do not require the patient to follow a lengthy daily regimen of heat and massage, but these remedies have thus far proven to be less effective, in most cases, than the heat-and-massage treatments. All pharmaceutical treatments for chronic conditions are problematic in the areas of drug allergies and sensitivities, interactions with other drugs and ongoing expense.

Additionally, surgical procedures have been developed using instruments to probe and express the meibomian glands. These procedures have been shown to offer some immediate results but are not practical for a patient to undergo on a weekly, monthly or sustained basis. This procedure also has to be done in a physician's office and with at least local anesthesia. It should be noted that all existing therapies are aimed at mid- to late-stage (symptomatic disease) and are augmented by the application of heat and massage.

For most people, once they develop meibomianitis, the condition lasts a lifetime. Untreated meibomian gland disease can lead to ocular infection and/or inflammation of the eyelids (referred to as posterior blepharitis). Posterior blepharitis, if untreated, can lead to corneal disease, which can lead to uncorrectable blurred vision and blindness in severe cases.

A number of devices have been invented that massage, heat and/or apply electrical microcurrent or sonic energy (which the present invention does not do) to various parts or the body, but none of them is specifically tailored to address the problem of meibomian gland disease. For example, U.S. Pat. No. 4,387,707 (Polikoff, 1983) discloses an eye treatment device that applies a fluctuating massaging force against the eye through a flexible wall in a chamber that contains a fluid maintained under a fluctuating pressure. This device does not involve heating of the eyelid.

U.S. Pat. No. 4,918,818 (Hsieh, 1990) describes a multipurpose shaver with a face massaging component. In order to use the face massaging component, the razor holder is detached from the body of the device, and the face massaging component is attached to the body of the device where the razor holder had been. This device does not involve a heating element.

U.S. Pat. No. 6,275,735 (Jarding et al., 2001) involves an apparatus for electrical microcurrent stimulation therapy of a body part. This invention is intended to provide electrical microcurrent stimulation around an eye to combat visual system diseases such as age-related mascular degeneration (AMD). The inventors claim that microcurrent stimulation will help rejuvenate the cells in the retina to slow or stop degeneration of the eye due to AMD. This invention does not involve any kind of a plate over the eyelid, nor does it involve heating. In a preferred embodiment, the electrical microcurrent is applied with a probe tip comprised of a cotton swab moistened or dampened with a conductive gel.

U.S. Pat. No. 7,069,084 (Yee, 2006) discloses a method for treating meibomianitis by massaging the muscle fibers in the eyelid that express the meibomian gland. The device is intended to cause the meibomian glands to expel any obstructing plugs in the meibomian glands. According to the inventors, the obstructing plug may be composed of hardened lipids (as described above), cellular debris or some combination thereof. The invention involves the placement of electrical contacts on the eyelid and the application of an electrical current to the eyelids via the electrical contacts, which in turn induces muscular contractions within the eyelid. Unlike the present invention, this particular invention does not try to prevent the hardened lipids from occurring.

U.S. Pat. No. 7,122,013 (Liu, 2006) describes an eye massage device comprising a mask with left and right portions and left and right diaphragms in each eye portion. The mask is connected to a pneumatic-powered cylinder assembly via a plastic tube. The pneumatic-powered cylinder assembly comprises a cylinder that alternately delivers compressed air to the mask and draws air from the mask. In this manner, the eyes are massaged. In one embodiment, spacers are located between the diaphragms and the eyes as a means for absorbing tears secreted by the eyes during operation. This device is not handheld, and it does not provide heat to the eyelid.

U.S. Pat. No. 7,384,405 (Rhoades, 2008) involves a cosmetic instrument with a number of different interchangeable heads. These heads include abrasive attachments, oxygenating attachments, brush attachments, thermal attachments, and light radiating attachments. These various types of treatment attachments are moved over an area of skin and/or body part by the user manipulating the handle and also by a motion generator that moves the head portions. The motion generator may move the attachments by vibrating, spinning, oscillating, or propagating sonic waves through the head portions. The purpose of the thermal attachment is to facilitate the application of a cosmetic composition or solution onto the skin. The thermal attachment is moved over an area of skin or a body part in "upward circular or randomly directed strokes" until the composition or solution has been worked into, cleaned, and/or polished the skin or body part. This device is not specifically tailored for treatment of an eyelid disorder.

U.S. Pat. No. 7,637,878 (Lin, 2009) discloses an eye massaging device with built-in air pump and actuation elements, an inflatable fomentation member, and a belt member to which the main member and fomentation member are attached. The main member contains a number of slidably engaged pieces that elastically expand along with the belt member when the device is tied around a user's head. The fomentation member is shaped like an eyeshade and comprises a first outer piece, a second outer piece, an air bag and a thin heating element. The air pump and leakage valve inflate and deflate the air bag to press the warm heating element against the eyes with various levels of pressure. This device treats both eyes at once and would not be effective in treating a single eyelid.

U.S. Patent Application Pub. No. 2002/0156402 (Woog et al.) describes a device that applies sonic energy to various parts of the body for therapeutic purposes. The device comprises an applicator end at which a predetermined amplitude is generated under applied loads. This device does not involve massage or heating of the eyelid.

U.S. Patent Application Pub. No. 2008/0200848 (Avni) involves a vibrating device that the inventor claims may be applied directly to a closed eyelid. This invention does not involve the application of heat to the eyelid, and the application does not include a single figure showing what the device would look like as applied to the eyelid.

None of the above inventions combines both heat and massage to effectively treat meibomian gland disease. What is needed is a handheld device that is easy to use, mechanically configured for placement over an eyelid, and that accomplishes both the thermostatically controlled heating and massaging of the eyelid at the same time. Accordingly, it is an object of the present invention to provide a handheld, battery-operated device with an oscillating, curved plate (for placement over the eyelid) that has a thermostatically controlled heating element within it. The oscillating motion of the curved plate applies a massaging action to the eyelid, and the heater is preferably controlled to achieve the optimum temperature. The present invention simultaneously liquefies and mobilizes the lipids in the meibomian glands, thereby causing them to move toward the gland orifices. With regular use, these oils remain less viscous, and the tear quality improves.

Recent research has concluded that meibomianitis is a condition that affects a vast number of individuals; some authors cite numbers as high as thirty percent of the population at fifty years of age. Researchers also agree that the condition becomes more common with age, which means that the percentages increase with an aging population. The disease is asymptomatic for some period of time—months to years—but almost always progresses. Eye physicians are well aware of this fact and the need to begin treatment as early as possible to alleviate damage from chronic disease. The very fact that the disease, in its early stages, is asymptomatic, coupled with the fact that treatments to date have their drawbacks or contraindications, leads doctors to allow the condition to go untreated until it becomes symptomatic and damage is done. In the later stages of the disease, treatment is more complex, costly and less-effective. The present invention will allow physicians to direct patients to a treatment method that is noninvasive, simple to use, and should provide years of service without ongoing expense.

In addition to meibomian gland dysfunction, other more acute eyelid conditions, which can occur at any age, are treated with warm massage. They too could be treated with the present invention; such common conditions as hordeolum and chalazion fall into this category.

BRIEF SUMMARY OF THE INVENTION

The present invention is a device for stimulating the meibomian glands of the eyelid comprising: a handle; a head that is non-removable and integral to the handle, the head comprising an eyepiece that oscillates to provide a massaging action to an eyelid and that comprises a front end that is concave in shape to fit over an eyelid; a heater located inside of the eyepiece; a temperature sensor located inside of the eyepiece, wherein the temperature sensor causes the eyepiece to heat to a predetermined temperature and then stop heating; and a charging base that supplies power to a motor that causes the eyepiece to oscillate, wherein the motor comprises a motor shaft.

In a preferred embodiment, the device further comprises a switch that allows the eyepiece to oscillate with or without heating. Preferably, the handle comprises a light emitting diode that indicates to a user whether the batteries are being charged and whether the eyepiece is heating.

In yet another preferred embodiment, oscillation of the eyepiece is effectuated by an oscillation assembly located within the head and comprising: a first stationary arm extending inward from an inner wall of the head; a rotating wheel that is connected to a rotating shaft that is in turn connected to the motor shaft; a second stationary arm extending inward from the inner wall of the head directly opposite the first stationary arm, the second stationary arm comprising a horizontal slot; and a connecting member with a first horizontal extension that is inserted into an aperture located off-center on the rotating wheel and a second horizontal extension that is inserted into the horizontal slot in the second stationary arm, wherein the connecting member comprises a center and pivots about a shaft that extends through an aperture in the center of the connecting member and that is fixedly attached to the eyepiece; wherein as the motor shaft rotates, the rotating shaft also rotates, causing the rotating wheel to rotate, the first extension on the connecting member to rotate in a circular motion, the second extension to move laterally within the slot on the second stationary arm, and the connecting member to pivot about the shaft that extends through the center of the connecting member, thereby causing the eyepiece to oscillate in an elliptical path.

In a preferred embodiment, the eyepiece further comprises an eyepiece cover that surrounds the front end of the eyepiece and that is comprised of a soft elastomer or silicone.

In yet another embodiment, the present invention is a method for stimulating the meibomian glands of the eyelid comprising: providing a device with a handle and a head that is non-removable and integral to the handle, the head comprising an eyepiece that oscillates to provide a massaging action to an eyelid; using a heater and temperature sensor located inside of the eyepiece to heat the eyepiece to heat to a predetermined temperature and maintain it the eyepiece at the predetermined temperature; using a motor located inside of the handle and to cause the eyepiece to oscillate; and applying the eyepiece to an eyelid of a user.

REFERENCE NUMBERS

Figure 1:
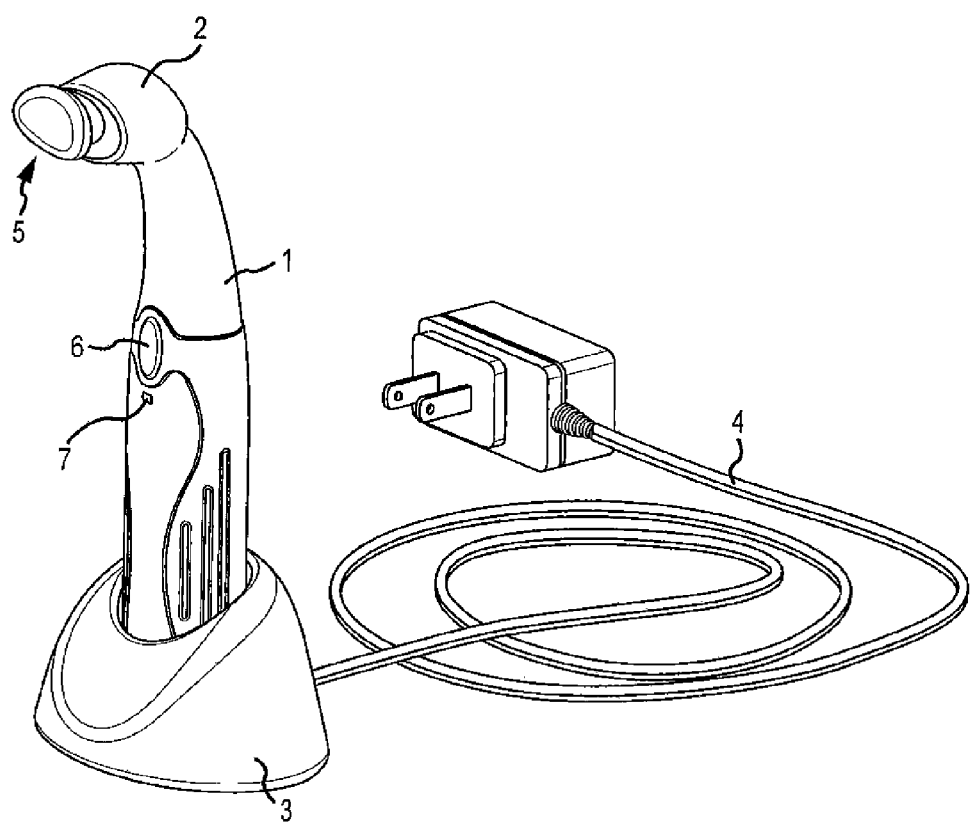
FIG. 1 is a perspective view of the present invention.

1 Handle
2 Head
2a Inner wall (of head)
3 Charging base
3a Collar
4 Power cord
5 Eyepiece
5a Eyepiece cover (on front end of eyepiece)
5b Front end (of front portion of eyepiece)
5c Front portion (of eyepiece)
5d Rear portion (of eyepiece)
6 Switch
7 LED
8 Outer base charge coupling device
9 Inner base charge coupling device
10 Vertical extension (from inner base charge coupling device)
11 Printed circuit board
12 Battery contact spring
13 Rechargeable battery
14 Motor
15 Clip (on printed circuit board for contacting the batteries)
16 Prong (on motor for connecting to printed circuit board)
17 Flexible shaft
18 First stationary arm
19 Rotating wheel
20 Second stationary arm
21 Horizontal slot (in second stationary arm)
22 Connecting member
23 First horizontal extension (of connecting member)
23a Aperture
24 Second horizontal extension (of connecting member)
25 Temperature sensor
26 Heater
27 Center shaft (of connecting member)
28 Motion path (of first extension)
29 Motion path (of second extension)
30 Motion path (of eyepiece)
31 Battery plus connection
32 Battery minus connection
33 First transformer input
34 Second transformer input
35 Temperature sensor voltage supply
36 Temperature sensor input
37 Return path to ground for temperature sensor
38 Positive heater connection
39 Negative heater connection
40 Positive motor connection
41 Negative motor connection
42a-42k Capacitors (comparator embodiment)
43a-43c Transistors (comparator embodiment)
44a-44f Resistors (comparator embodiment)
45 Inductor (comparator embodiment)
46a-46d Integrated circuits (comparator embodiment)
47 Diode bridge rectifier (comparator embodiment)
48 Diode (comparator embodiment)
49 Fuse (comparator embodiment)
50 Microcontroller
51a-51k Capacitors (microcontroller embodiment)
52a-52c Transistors (microcontroller embodiment)
53a-53e Resistors (microcontroller embodiment)
54 Inductor (microcontroller embodiment)
55a-55c Integrated circuits (microcontroller embodiment)
56 Diode bridge rectifier (microcontroller embodiment)
57 Diode (microcontroller embodiment)
58 Fuse (microcontroller embodiment)

DETAILED DESCRIPTION OF INVENTION

FIG. 1 is a perspective view of the present invention. As shown in this figure, the present invention is a handheld device that is preferably battery charged. Thus, the invention comprises a handle 1, a head 2, a charging base 3 and a power cord 4. The head 2 comprises a single eyepiece 5 that is placed over the eye (with the eyelid closed) and that provides a gentle massaging action to the eyelid. This gentle massaging action is caused by the oscillation of the eyepiece 5. In a preferred embodiment, the eyepiece 5 oscillates in an elliptical motion.

The handle 1 preferably comprises a switch 6, which, in a preferred embodiment, allows the massaging action of the eyepiece 5 to be activated either alone or in combination with heat. The power cord 4 supplies power to rechargeable batteries (not shown) located inside the handle 1. The handle 1 also preferably comprises a light emitting diode (LED) 7. In a preferred embodiment, the LED 7 is a dual LED with both a green LED and a red LED in the same light. The green LED indicates that the batteries are being charged. The red LED indicates that the unit is heating the eyepiece.

Figure 2:
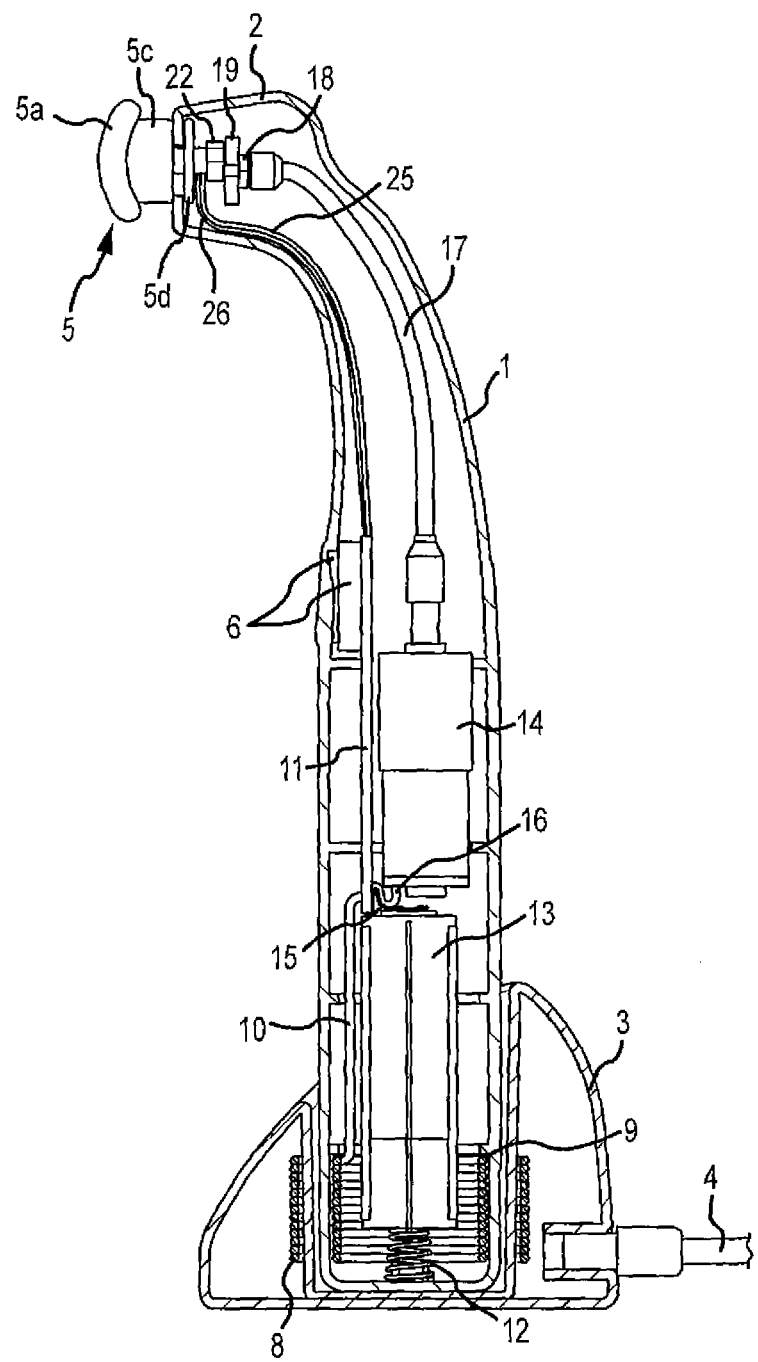
FIG. 2 is a section view of the present invention.

FIG. 2 is a section view of the present invention. As shown in this figure, inside the charging base 3 is an outer base charge coupling device 8, which is electrically coupled to an inner base charge coupling device 9. A collar 3a is situated between the outer and inner base charge coupling devices, which act together as an electrical transformer. The base charge coupling device plugs into an alternating current (AC) outlet via the power cord 4. Electrical current is transferred from the power cord to the outer base charge coupling device 8 and then from the outer base charge coupling device 8 to the inner base charge coupling device 9. The inner base charge coupling device 9 comprises a two-pronged vertical extension 10 that connects to the printed circuit board 11. The printed circuit board 11 comprises a charging circuit for the batteries.

Inside the bottom end of the handle 1 is a battery contact spring 12, which holds the batteries in place. The spring 12 also acts as an electrical conductor, allowing the electrical current to pass from the printed circuit board 11 to the plus side of the first battery, from the negative side of the first battery to the spring, through the spring, to the plus side of the other battery, and through the negative side of the second battery back to the printed circuit board—thereby forming a complete electrical circuit.

The handle 1 preferably houses two rechargeable batteries 13 and a motor 14. the motor 14 is preferably a low-voltage, low-current constant RPM (revolutions per minute) motor. The printed circuit board 11 comprises two clips 15, each of which contacts the top of one of the batteries 13. Extending from the bottom of the motor 14 are two prongs 16 that connect to the printed circuit board 11. As shown in this figure, the switch 6 is affixed to the printed circuit board 11.

In one embodiment, the motor shaft (not shown) of the motor 14 is connected to a flexible shaft 17, which extends from the top of the motor 14 to inside of the head 2 so that as the motor shaft rotates, the flexible shaft 17 also rotates. In an alternate embodiment (not shown), two non-flexible shafts connected by a first universal joint could be used in lieu of the flexible shaft. In the latter embodiment, the first shaft would be connected to the motor shaft, and the second shaft would be connected to the oscillation assembly inside the head 2. A second universal joint would be located at the point at which the second shaft connects to the oscillation assembly.

The oscillation assembly comprises a first stationary arm 18, a rotating wheel 19, a second stationary arm 20 with a horizontal slot 21, and a connecting member 22 with a first and second horizontal extension 23, 24. The oscillation assembly is shown in detail in FIGS. 4A-4D. The connecting member 22 is in turn attached to the eyepiece 5 so that as the connecting member 22 moves in an elliptical motion (caused by the rotating wheel 19 and the horizontal movement of the second horizontal extension 24 inside the horizontal slot 21 of the second stationary arm 20), the eyepiece 5 also moves in an elliptical motion. This mechanism is explained more fully below in connection with FIGS. 5A-4F.

Extending from the printed circuit board 11 to the eyepiece 2 are a temperature sensor 25 and a heater 26, which is preferably both insulated and flexible. The heater 26 is preferably a standard polyimide heater manufactured by Minco Products, Inc. of Minneapolis, Minn., and the temperature sensor 25 is preferably a TO-92, part number LM19, manufactured by National Semiconductor of Santa Clara, Calif. In an alternate embodiment, the heater and sensor could be integrated into a single part. Preferably, the distal ends (i.e., the ends farthest from the printed circuit board) of both the heater 26 and the temperature sensor 25 are embedded in the front portion 5c of the eyepiece 5 behind the eyepiece cover 5a (see FIG. 3).

Figure 3:
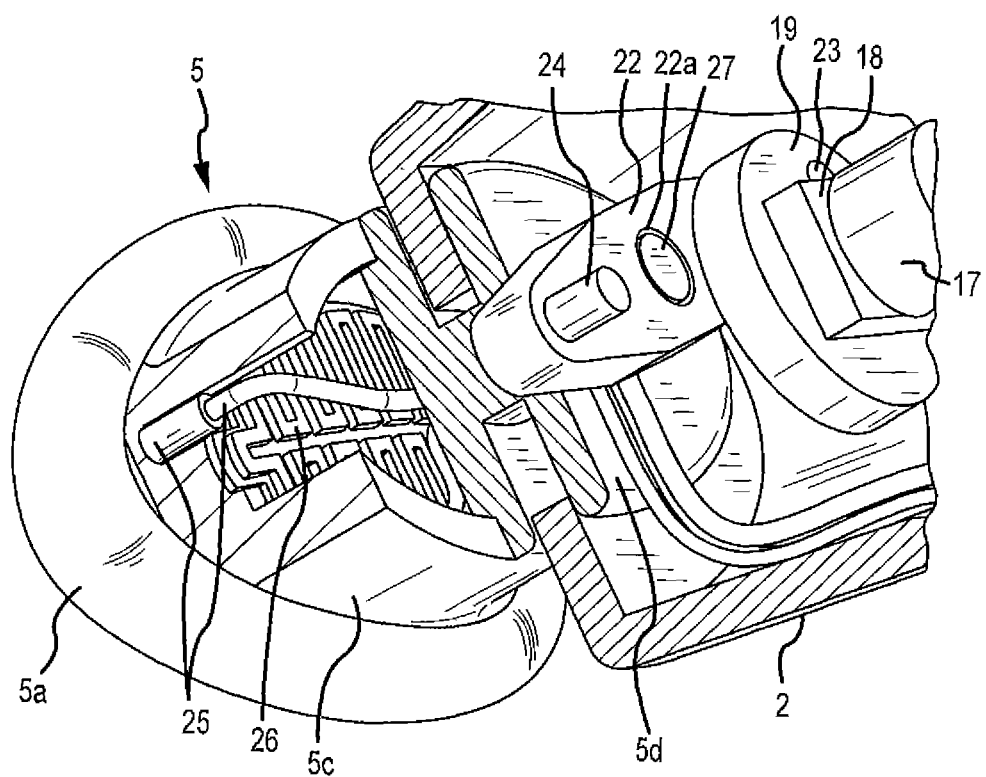
FIG. 3 is a perspective section view of the eyepiece of the present invention showing the location of the heater and temperature sensor.
Figure 4:
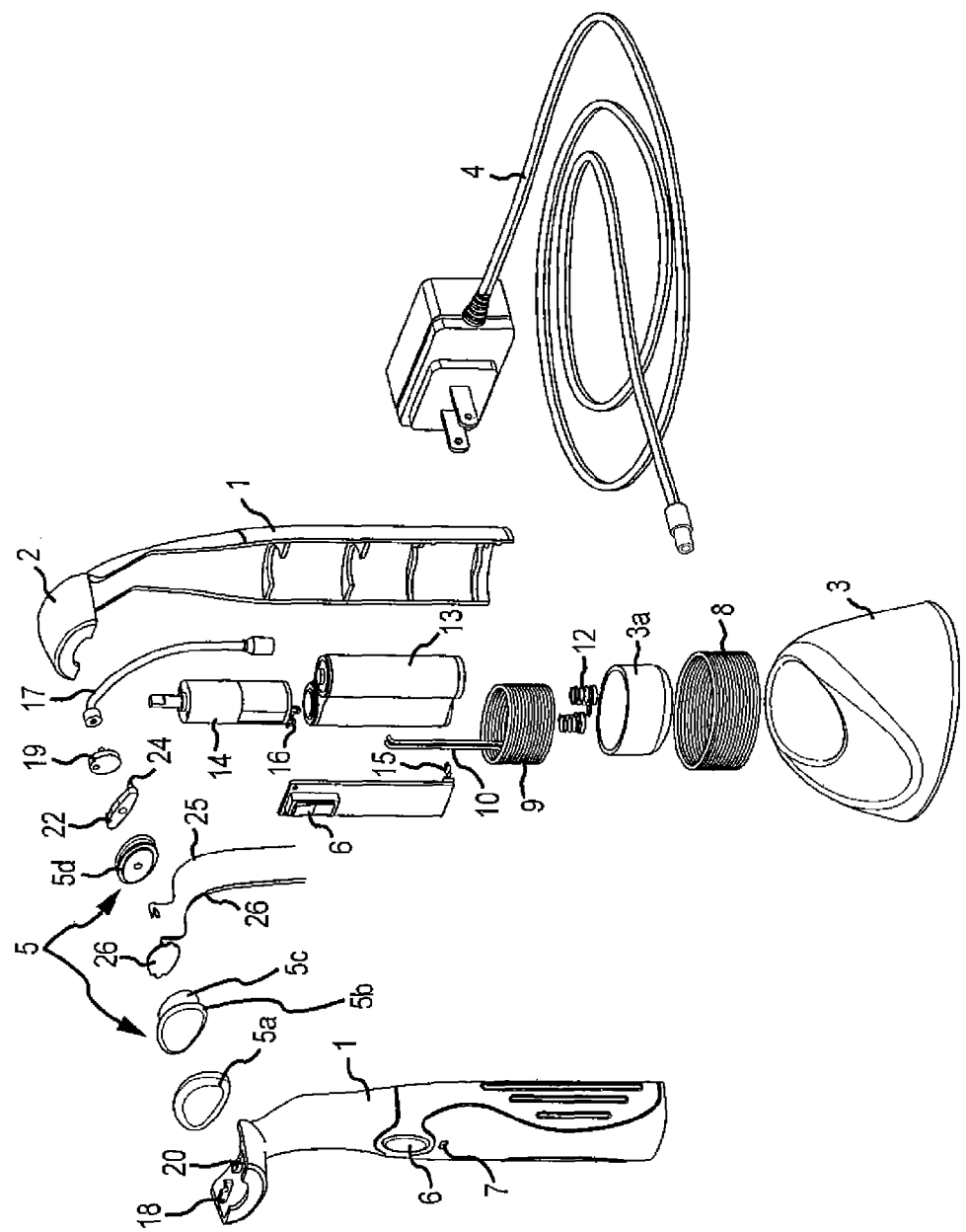
FIG. 4 is an exploded view of the present invention.

The eyepiece cover 5a surrounds the front end 5b of the front portion 5c of the eyepiece 5 and is preferably made of a soft elastomer or silicone. In a preferred embodiment, the front end 5b of the front portion 5c of the eyepiece is oval in shape and concave to fit comfortably over the eyelid. The eyepiece also comprises a rear portion 5d that is separate from the front portion 5c and that abuts up against the back end of the front portion 5c of the eyepiece when the device is fully assembled, as shown in FIGS. 2, 3 and 4. FIG. 4 is an exploded view of the present invention showing all of the parts discussed above.

In a preferred embodiment, the head 2 is non-removable and integral to the handle 1. The head 2 comprises the eyepiece 5 and oscillation assembly, which is described above in connection with FIG. 2 and below in connection with FIGS. 5A-5F.

Figure 5A:
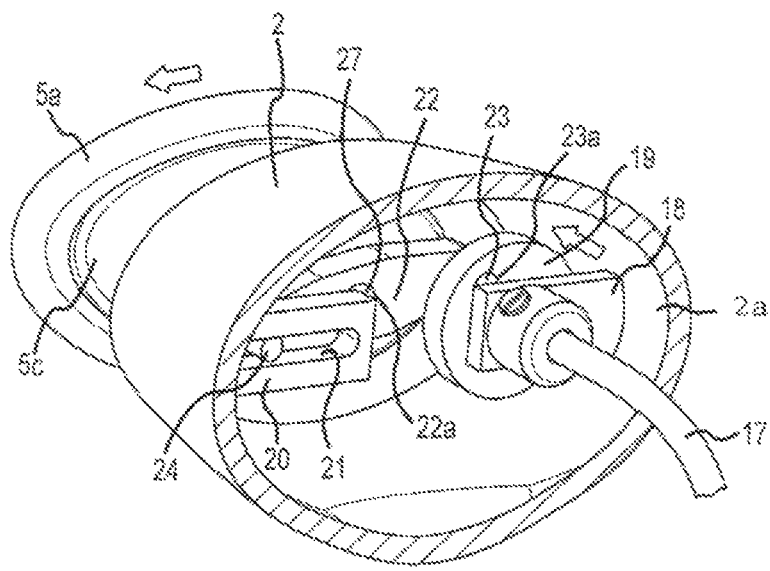
FIG. 5A is a first detail section view of the oscillation assembly of the present invention.

FIG. 5A is a first detail perspective section view of the oscillation assembly of the present invention. As shown in this figure, the flexible shaft 17 is connected to a first stationary arm 18 that extends inward from the inner wall 2b of the head 2. The flexible shaft 17 extends through an aperture (not shown) in the first stationary arm 18 and is connected to the center of the rotating wheel 19 such that when the flexible shaft 17 rotates, the rotating wheel 19 also rotates. The first extension 23 on one end of the connecting member 22 is inserted into an aperture 23a in the rotating wheel 19; this aperture 23a is off-center on the rotating wheel 19 so that as the rotating wheel 19 rotates, the end of the connecting member 22 to which the first extension 23 is attached also moves in a circular motion.

FIG. 5A also shows the second stationary arm 20, which extends inward from the inner wall 2b of the head 2 directly opposite the first stationary arm 18. The second extension 24 on the other end of the connecting member 22 (that is, the end opposite the first extension 23) is inserted into the horizontal slot 21 in the second stationary arm 20. Thus, as the first extension 23 rotates in a circular motion, the second extension 24 moves laterally back and forth within the horizontal slot 21.

The center of the connecting member 22 pivots about a shaft 27 that extends through an aperture 22a in the center of the connecting member 22 and that is fixedly attached to the eyepiece 5. In this manner, as the flexible shaft 17 rotates, causing the rotating wheel 19 to rotate, the first extension on the connecting member 22 to rotate in a circular motion, and the second extension 24 to move laterally within the slot 21 on the second stationary arm 20, the connecting member 22 pivots about the shaft 27, thereby causing the eyepiece 5 to oscillate in an elliptical path.

Figure 5B:
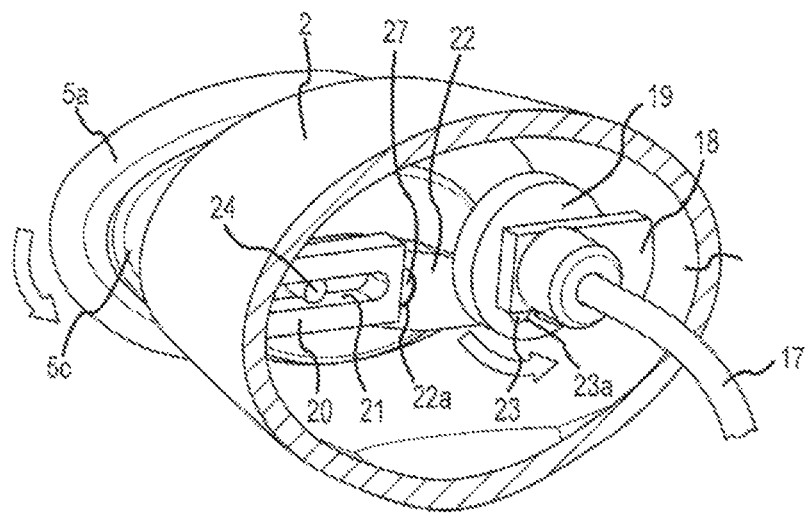
FIG. 5B is a second detail perspective section view of the oscillation assembly of the present invention.
Figure 5C:
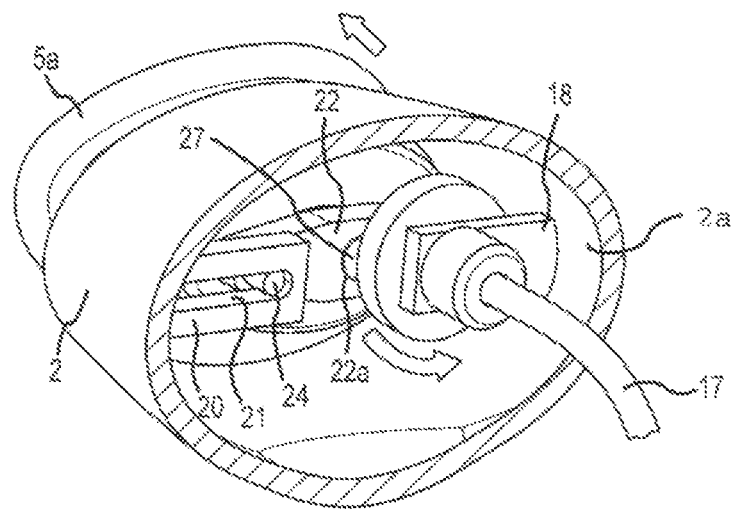
FIG. 5C is a third detail perspective section view of the oscillation assembly of the present invention.
Figure 5D:
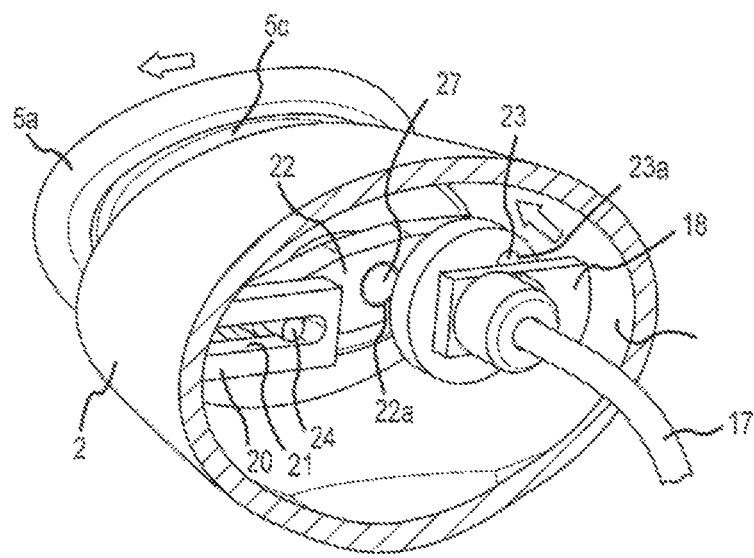
FIG. 5D is a fourth detail perspective section view of the oscillation assembly of the present invention.
Figure 5E:
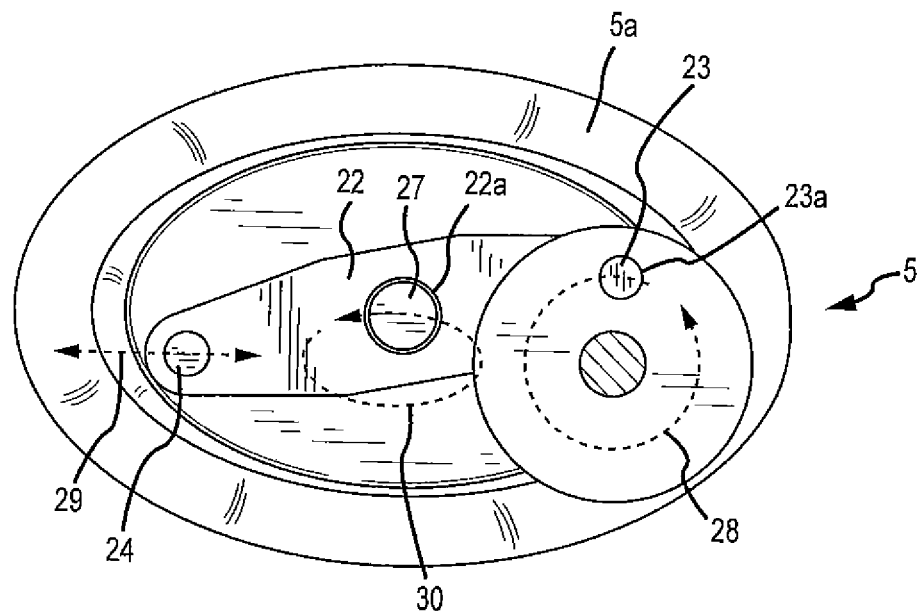
FIG. 5E is an illustration of the motion paths of the oscillation assembly of the present invention.
Figure 5F:
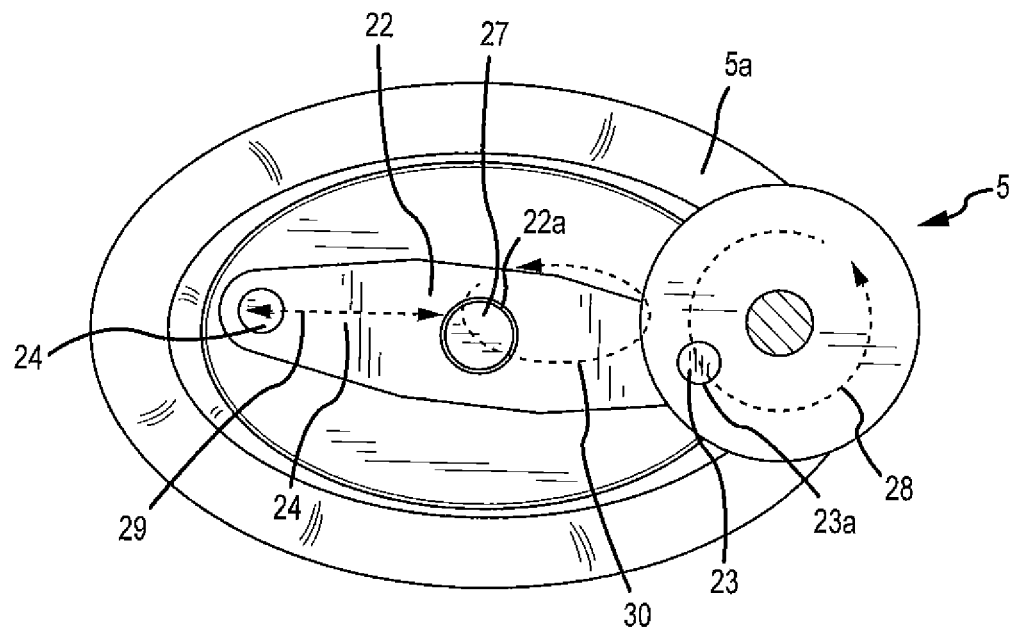
FIG. 5F is an illustration of the motion paths of the oscillation assembly of the present invention.

It is the combination of the circular motion on one end of the connecting member 22 and the horizontal motion on the other end of the connecting member 22, combined with the fact that the connecting member 22 is able to pivot about its center shaft 27, which is fixedly connected to the eyepiece 5, that results in the eyepiece moving in an elliptical direction. FIGS. 5B-5D illustrate the motion of the various parts of the oscillating assembly as the flexible shaft 17 rotates. FIGS. 5E and 5F illustrate the paths of motion of the first extension 28, second extension 29 and eyepiece 30, respectively. The flexible shaft 17, first stationary arm 18 and second stationary arm 20 have been omitted from FIGS. 5E and 5F for clarity.

With regard to the electronic components of the invention, in one embodiment, the printed circuit board 11 comprises a comparator circuit. In an alternate embodiment, the printed circuit board 11 comprises a microcontroller in lieu of the comparator circuit. Schematic diagrams of these two embodiments are provided in FIGS. 6 and 9, respectively. A comparison of these two figures reveals that the only difference between the two embodiments is the inclusion of the comparator circuit (comprising two resistors, a reference and a comparator) in the first embodiment and the inclusion of a microcontroller in lieu of the comparator circuit in the second embodiment. The former will be referred to herein as the "comparator embodiment," and the latter will be referred to herein as the "microcontroller embodiment." The present invention is not limited to any particular method of controlling the temperature sensor and heater, but these two methods represent preferred embodiments.

Figure 6:
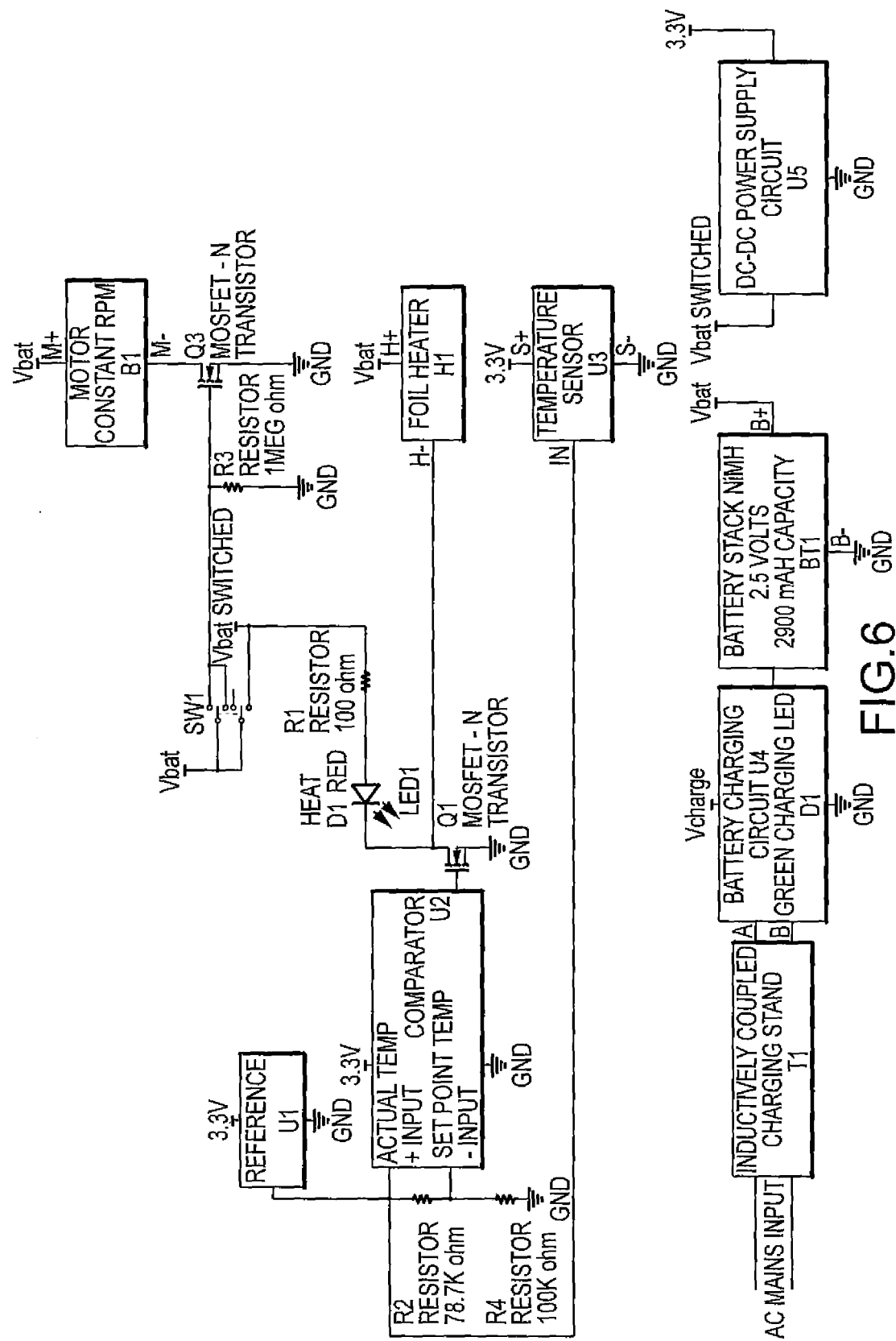
FIG. 6 is a schematic diagram of the switch embodiment of the present invention.

Referring to FIG. 6, the inductively coupled charging stand includes a transformer made from the outer base charge coupling device 8 and the inner base charge coupling device 9, the diode bridge rectifier 47, the diode 48, the fuse 49 and capacitors 42j and 42k. The battery charging circuit includes integrated circuit 46c, LED 7, capacitors 42d, 42f and 42i, resistors 44f and 44d and transistor 43b. The DC-DC power supply circuit includes integrated circuit 46d, capacitor 42g, capacitors 42b, 42c and 42h and inductor 45. The temperature sensor includes integrated circuit 25 (which is physically located in the eyepiece) and capacitor 42e. The reference includes integrated circuit 46a and capacitor 42a. The comparator circuit includes integrated circuit 46b and resistors 44a and 44c. The foil heater circuit includes the heater 26, transistor 43a, LED 7 and resistor 44e. The motor circuit includes the motor 14, transistor 43c, switch 6 and resistor 44b.

Figure 9:
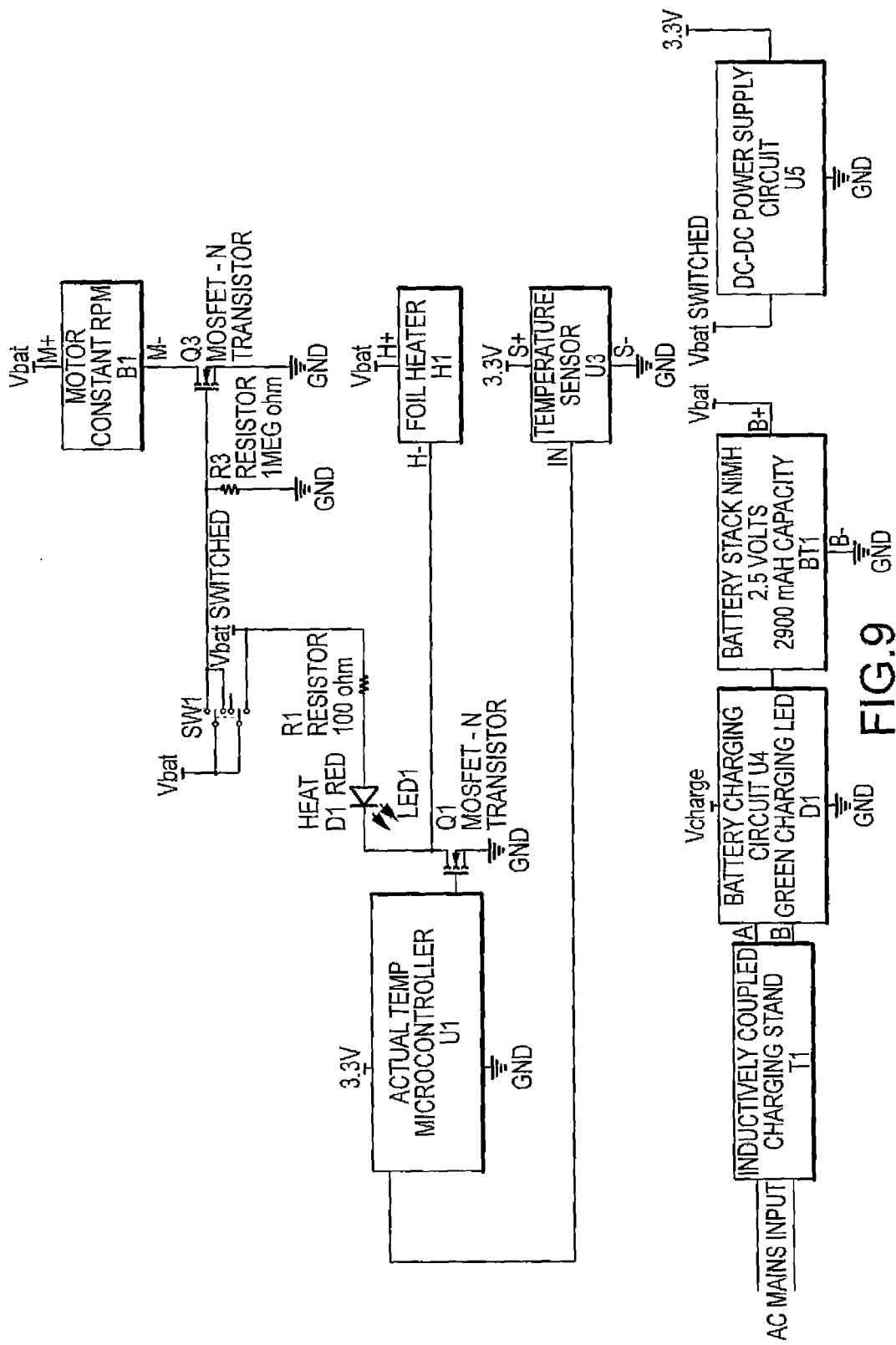
FIG. 9 is a schematic diagram of the microcontroller embodiment of the present invention.

Referring to FIG. 9, the inductively coupled charging stand includes a transformer made from the outer base charge coupling device 8 and the inner base charge coupling device 9, the diode bridge rectifier 56, the diode 57, the fuse 58 and capacitors 51j and 51k. The battery charging circuit includes integrated circuit 55b, LED7, capacitors 51d, 51f and 51i, resistors 53e and 53c and transistor 52b. The DC-DC power supply circuit includes integrated circuit 55c, capacitors 51b, 51c, 51g and 51h and inductor 54. The temperature sensor includes integrated circuit 25 (which is physically located in the eyepiece) and capacitor 51e. The microcontroller circuit includes the microcontroller 50, resistor 53b and capacitor 51a. The foil heater circuit includes the heater 26, transistor 52a, LED 7 and resistor 53d. The motor circuit includes motor 14, transistor 52c, switch 6 and resistor 53a.

The following description of the printed circuit board, its components and the configuration of those components is meant to describe a preferred embodiment. The present invention is not limited to any particular type of components or configuration of the printed circuit board, except as specifically claimed herein.

Figure 7:
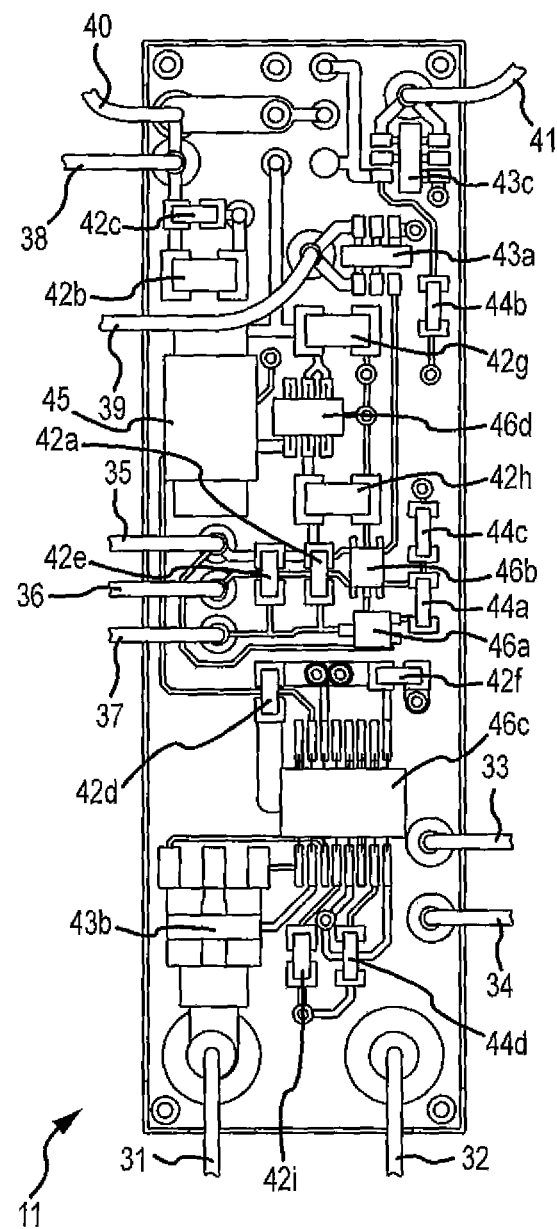
FIG. 7 is an illustration of the first layer of the printed circuit board of the switch embodiment of the present invention.
Figure 8:
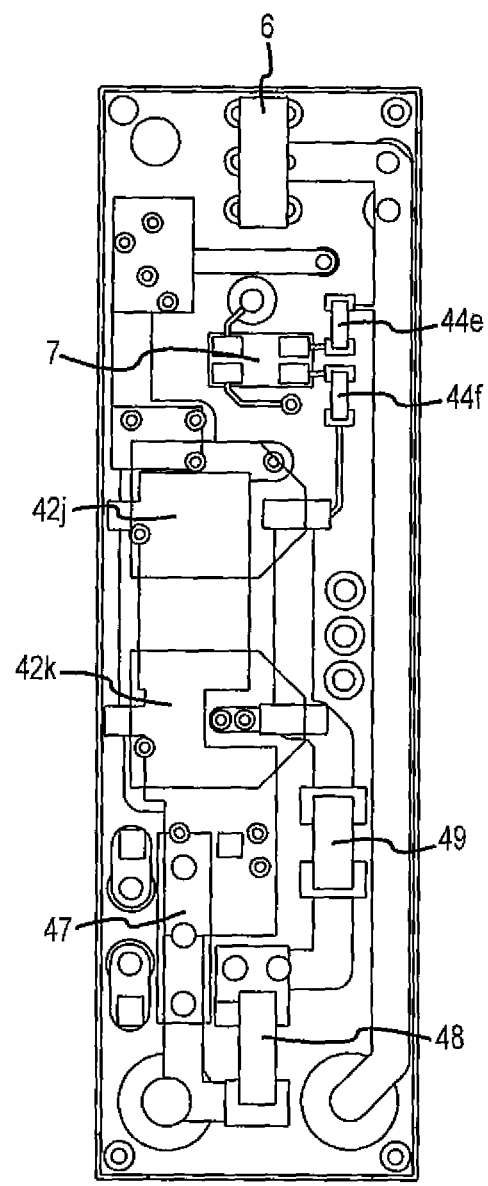
FIG. 8 is an illustration of the second layer of the printed circuit board of the switch embodiment of the present invention.

In a preferred embodiment, the printed circuit board comprises two layers. The first layer of the printed circuit board is shown in FIGS. 7 (comparator embodiment) and 10 (microcontroller embodiment), and the second layer of the printed circuit board is shown in FIGS. 8 (comparator embodiment) and 11 (microcontroller embodiment). The present invention is not limited to any particular configuration of the printed circuit board, and FIGS. 7, 8, 10 and 11 are meant to be exemplary only.

Referring to FIG. 7, the first layer of the printed circuit board 11, which would face the rear of the handheld device, comprises a battery plus connection 31, a battery minus connection 32, a first transformer input 33, a second transformer input 34, a temperature sensor voltage supply 35, a temperature sensor input 36, and a return path to ground for the temperature sensor 37. The printed circuit board 11 further comprises a positive heater connection 38, a negative heater connection 39, a positive motor connection 40 and a negative motor connection 41. Capacitors 42a, 42c, 42e and 42f are ceramic bypass capacitors and provide noise filtering. Capacitors 42b, 42d, 42g and 42h are tantalum bypass capacitors and provide noise filtering. Capacitor 42i is a ceramic capacitor and sets the charging time in the battery charger circuit.

Transistor 43a is a metal-oxide-semiconductor field-effect transistor (MOSFET) switch used to turn on and off the heater. Transistor 43b is a PNP transistor that provides charge current to the battery stack in the charging circuit. Transistor 43c is a MOSFET switch used to turn the motor on and off.

Resistors 44a and 44c are used to set the voltage at the negative input of the comparator circuit, and this voltage corresponds to the set point temperature. Resistors 44b is a pull-down resistor that places the gate of transistor 43c at a voltage of zero volts (ground) when there is no battery voltage (referred to as "Vbat" on FIGS. 6 and 9) input from the switch 6 to the gate of transistor 43c and ensures that transistor 43c is turned off, thereby causing the motor 14 to stop turning. Resistor 44d sets the charge current for the battery charging circuit.

The inductor 45 is used as part of the switching circuit that is inside of integrated circuit 46c. Integrated circuit 46a is a precision voltage reference that provides a very stable output voltage of 2.5 volts from a power supply of +3.3 volts. Integrated circuit 46b is a comparator circuit that is used to turn transistor 43a on and off at the appropriate time. Integrated circuit 46c is a stand-alone linear NiMH fast battery charger. Integrated circuit 46d is a boost regulator that provides an output voltage of +3.3 volts at up to 200 mA of current from a varying input voltage, Vbat switched provided by the battery stack. As used herein, the term "Vbat switched" means the voltage after switch 6 (SW1 on FIG. 6) and is the input to the DC-DC power supply circuit.

Referring to FIG. 8, the second layer of the printed circuit board, which would face the front of the handheld device, comprises the switch 6, a fifth resistor 44e and a sixth resistor 44f, a light-emitting diode 7, a tenth capacitor 42j and an eleventh capacitor 42k, a diode bridge rectifier 47, a diode 48 and a fuse 49. Resistors 44e and 44f provide current limiting for the LED 7. Capacitors 42j and 42k are electrolytic capacitors and are used as filtering capacitors for the charging voltage that supplies the battery charging circuit (referred to as "Vcharge" on FIGS. 6 and 9). Diode bridge rectifier 47 converts the incoming low voltage AC signal to a DC voltage. Diode 48 provides a clamping function to limit the DC voltage available on the Vcharge voltage supply. The fuse 49 is a resettable fuse that provides overcurrent protection for the device.

Figure 10:
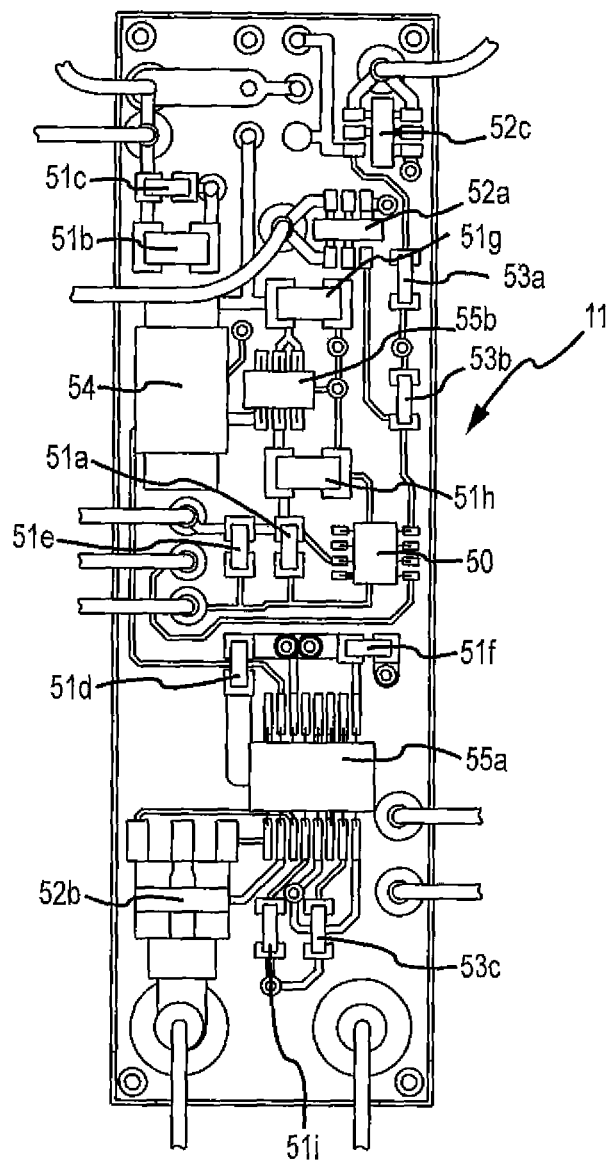
FIG. 10 is an illustration of the first layer of the printed circuit board of the microcontroller embodiment of the present invention.
Figure 11:
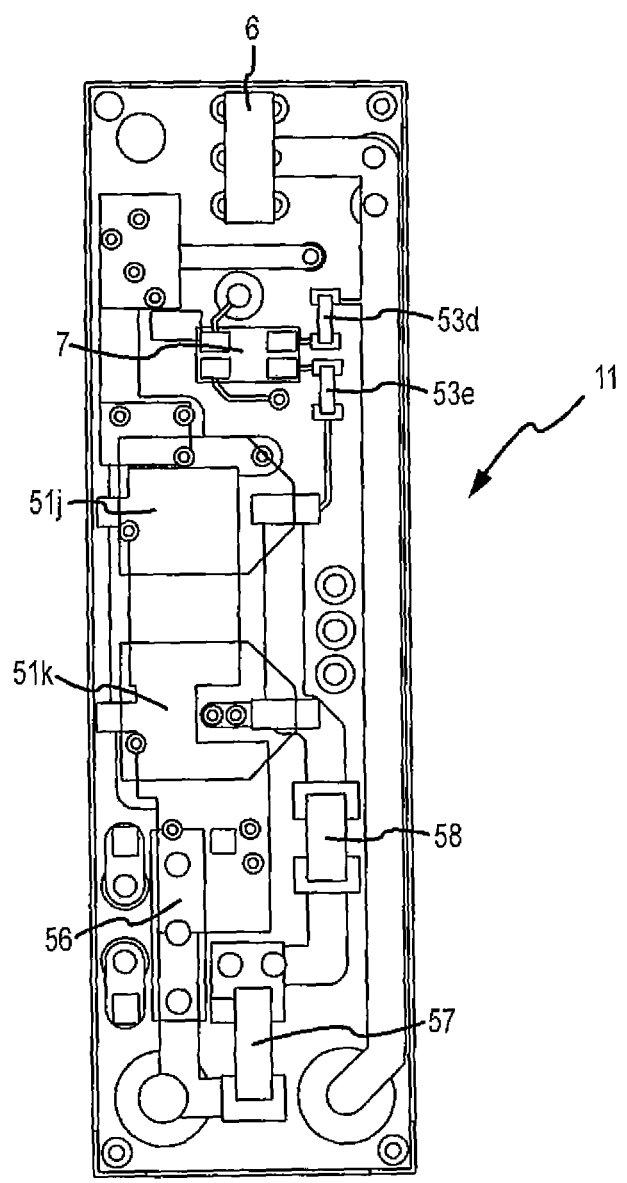
FIG. 11 is an illustration of the second layer of the printed circuit board of the microcontroller embodiment of the present invention.

FIGS. 10 and 11 show, respectively, the first and second layers of the printed circuit board in the microcontroller embodiment. Integrated circuit 50 is an MC9S08QG8 8-bit Freescale microcontroller that uses one input as an analog input to measure the actual temperature voltage provided from the temperature sensor 25 on temperature sensor input 36. The actual temperature voltage is converted to a digital representation inside the microcontroller and compared to a programmed digital representation of the set point temperature inside the microcontroller. The microcontroller uses one digital output line to then control transistor 52*a*.

Referring to FIGS. 10 and 11, capacitors 51*a*-51*k* of the microcontroller embodiment are the same as capacitors 42*a*-42*k* of the comparator embodiment. Transistors 52*a*-52*c* of the microcontroller embodiment are the same as transistors 43*a*-43*c* of the comparator embodiment. Resistors 53*a*, 53*c*, 53*d* and 53*e* of the microcontroller embodiment are the same as resistors 44*b*, 44*d*, 44*e* and 44*f*, respectively, of the comparator embodiment; resistors 44*a* and 44*c* (shown in FIG. 6 as R2 and R4) are used only in the comparator embodiment. Conversely, the microcontroller embodiments includes one resistor 53*b* that is not part of the comparator embodiment; thus, the microcontroller embodiment has one fewer resistor than the comparator embodiment. Resistor 53*b* is used as a pull-down resistor that places the gate of transistor 52*a* at a voltage of zero volts (ground) when there is no input from the microcontroller 50 to the gate of transistor 52*a* and ensures that transistors 52*a* is turned off, thereby causing the heater 26 to stop heating.

The inductor 54 of the microcontroller embodiment is the same as the inductor 45 of the comparator embodiment. Integrated circuits 55*a* and 55*b* of the microcontroller embodiment are the same as integrated circuits 46*c* and 46*d* of the comparator embodiments (integrated circuits 46*a* and 46*b* are used only in the comparator embodiment). Note that the diode bridge rectifier is shown as reference number 56 on FIG. 11; the diode is shown as reference number 57 on FIG. 11; and the fuse is shown as reference number 58 on FIG. 11.

In the microcontroller embodiment, the microcontroller is programmed to activate the heater 26 when the switch 6 is turned on (and assuming the temperature of the eyepiece is less than a set point temperature) and to turn the heater off when the temperature sensor 25 senses that the temperature in the eyepiece has reached or exceeded the set point temperature. In a preferred embodiment, the set point temperature is 104 degrees Fahrenheit.

In the comparator embodiment, the comparator circuit serves the same function as the microcontroller in that it turns the heater on when the temperature in the eyepiece is less than the set point temperature, and it turns the heater off when the temperature in the eyepiece is greater than the set point temperature. The comparator circuit consists of integrated circuit 46*b* and resistors 44*a*, 44*c*. Resistors 44*a*, 44*c* are used to set the voltage at the negative input of the comparator circuit, and this voltage corresponds to the set point temperature. The resistors 44*a*, 44*c* use the very stable reference circuit 46*a* voltage to generate the set point temperature voltage.

The desired set point temperature is 104° F. (or 40° C.), and the following equation (from the sensor manufacturer's data sheet) is used to calculate the temperature sensor output voltage:

$$VO = -11.69 \text{ mV}/°C. \times T + 1.8663 \text{ V}$$

where VO is the temperature sensor output voltage, and T is the set point temperature. Using a value of 40° C. for value T, the temperature sensor output voltage is 1.3987 volts, which is the voltage that will be provided to the set point temperature input of the comparator circuit.

The above formula is used to calculate the temperature sensor output voltage. The formula below is used to calculate the set point temperature input voltage to the comparator circuit. These two values need to be the same in order for the comparator circuit to control the temperature at the eyepiece to the desired temperature.

Using a reference voltage of 2.5 volts, a value of 78.7K ohms for resistors 44*a* (R1), and a value of 100K ohms for resistor 44*c* (R2), the set point temperature voltage is calculated according to the following equation:

$$V_{set\,point\,temperature} = 2.5(R2)/(R1+R2)$$

In this example, the set point temperature voltage is 1.3989 volts, which corresponds to a desired temperature of 104° F. The voltage at the positive input of the comparator circuit is the actual temperature input and is provided by the temperature sensor input 36 from temperature sensor 25. The comparator circuit uses the actual temperature voltage and the set point temperature voltage to determine when to turn on and off transistor 43*a*.

Although the preferred embodiment of the present invention has been shown and described, it will be apparent to those skilled in the art that many changes and modifications may be made without departing from the invention in its broader aspects. The appended claims are therefore intended to cover all such changes and modifications as fall within the true spirit and scope of the invention.

We claim:

1. A device for stimulating the meibomian glands of the eyelid comprising:
    (a) a handle that contains batteries, a printed circuit board and a motor;
    (b) a head that is non-removable and integral to the handle, the head comprising an oscillation assembly and an eyepiece that oscillates in an elliptical motion to provide a massaging action to an outside of an eyelid, the eyepiece comprising:
        (i) a front portion comprising a front end, wherein the front end is concave in shape to fit over the outside of an eyelid, and a rear end; and
        (ii) a rear portion, the rear portion being separate from the front portion and abutting up against a back end of the front portion when the device is fully assembled;
    (c) a heater that is insulated and flexible and that extends from the printed circuit board to the eyepiece, the heater comprising a distal end;
    (d) a temperature sensor that extends from the printed circuit board to the eyepiece, the temperature sensor comprising a distal end, wherein the temperature sensor causes the eyepiece to heat to a predetermined temperature not to exceed about one hundred four degrees Fahrenheit and then stop heating; and
    (e) a charging base that supplies power to the motor, wherein the motor comprises a motor shaft, and wherein the motor causes the eyepiece to oscillate in an elliptical motion;
    wherein the distal end of the header and the distal end of the temperature sensor are embedded in the front portion of the eyepiece;
    wherein the oscillation assembly comprises:
    (a) a first stationary arm extending inward from an inner wall of the head;
    (b) a rotating wheel that is connected to a rotating shaft that is in turn connected to the motor shaft;

(c) a second stationary arm extending inward lfrom the inner wall of the head directly opposite the first stationary arm, the second stationary arm comprising a horizontal slot; and
(d) a connecting member with a first horizontal extension that is inserted into an aperture located off-center on the rotating wheel and a second horizontal extension that is inserted into the horizontal slot in the second stationary arm, wherein the connecting member comprises a center and pivots about a shaft that extends through an aperture in the center of the connecting member and that is fixedly attached to the eyepiece;
wherein as the motor shaft rotates, the rotating shaft also rotates, causing the rotating wheel to rotate, the first extension on the connecting member to rotate in a circular motion, the second extension to move laterally within the horizontal slot on the second stationary arm, and the connecting member to pivot about the shaft that extends through the center of the connecting member, thereby causing the eyepiece to oscillate in an elliptical path.

* * * * *